United States Patent [19]

Saitou et al.

[11] Patent Number: 5,144,066
[45] Date of Patent: Sep. 1, 1992

[54] METHOD OF PRODUCING NAPHTHALENEDICARBOXYLIC ACIDS AND DIARYLDICARBOXYLIC ACIDS

[75] Inventors: Noboru Saitou, Takatsuki; Koichi Hirota; Ren Hasebe, both of Suita; Norimasa Okuda, Kyoto; Ikuyo Katsumi, Osaka, all of Japan

[73] Assignee: Nippon Shokubai Co., Ltd., Osaka, Japan

[21] Appl. No.: 720,682

[22] Filed: Jun. 25, 1991

[30] Foreign Application Priority Data

Jun. 26, 1990 [JP] Japan ................... 2-167313
Jun. 26, 1990 [JP] Japan ................... 2-167314
Dec. 25, 1990 [JP] Japan ................... 2-405852

[51] Int. Cl.$^5$ .................................. C07C 51/265
[52] U.S. Cl. ...................... 562/416; 562/417; 562/488
[58] Field of Search .............. 562/416, 417, 488

[56] References Cited

U.S. PATENT DOCUMENTS 4,750,786 6/1988 Sanchez et al. ............... 562/416
4,794,195 12/1988 Hayashi et al. ................ 562/414
4,970,338 11/1990 Matsuda et al. ............... 562/416

OTHER PUBLICATIONS

"Effect of Pyridine on Cobalt Bromide Catalyzed Oxidation of P-Xylene in Various Solvents", Oxidation Communications 3, Nos. 3-4, 303-314 (1983).

*Primary Examiner*—Jose G. Dees
*Assistant Examiner*—Vera C. Clarke
*Attorney, Agent, or Firm*—Birch, Stewart, Kolasch & Birch

[57] ABSTRACT

A method of producing naphthalenedicarboxylic acids by the oxidation of dialkyl-substituted naphthalene with a gas containing molecular oxygen under liquid phase conditions in an organic solvent and in the presence of a catalyst comprising copper and bromine, or a catalyst comprising copper, bromine and at least one kind of element/compound selected from the group of consisting of amine compounds and heavy metallic elements which are vanadium, manganese, iron, cobalt, nickel, palladium and cerium. And a method of producing diaryldicarboxylic acids by the oxidation of dialkyl-substituted diaryl compounds with a gas containing molecular oxygen in an organic solvent and in the presence of the same catalyst. These methods permit high yields of naphthalenedicarboxylic acids of high purity and of diaryldicarboxylic acids of high purity with the use of small amounts of catalyst.

24 Claims, No Drawings

METHOD OF PRODUCING NAPHTHALENEDICARBOXYLIC ACIDS AND DIARYLDICARBOXYLIC ACIDS

The present invention relates to a method for producing naphthalenedicarboxylic acids and diaryldicarboxylic acids by the oxidation of dialkyl-substituted naphthalene compounds and of dialkyl-substituted diaryl compounds with a gas containing molecular oxygen under liquid-phase conditions in an organic solvent.

BACKGROUND OF THE INVENTION

Conventionally, it is known that films and various by-products, which is formed by reacting polyethylene naphthalate made of 2,6-naphthalenedicarboxylic acid and ethylene glycol, have improved mechanical strength, heat-resistance, size stability etc. relative to those produced from polyethylene terephthalate, which is formed from terephthalic acid.

As for the production of 2,6-naphthalenedicarboxylic acid (hereinafter referred to as 2,6-NDA), the following methods are known. (A) Methods of producing 2,6-NDA by the oxidation of dialkyl-substituted naphthalene with molecular oxygen in an acetic acid solvent in the presence of a catalyst comprising cobalt, manganese and bromine (Japanese Publication for Examined Patent applications No. 48-27318/1973, No. 56-3337/1981, Japanese Publication for Unexamined Patent applications No. 61-140540/1986, No. 62-212345/1987, No. 64-3148/1989, No. 1-160943/1989 and No. 1-287055/1989).

Meanwhile, for the production of aromatic carboxylic acids, (B) a method disclosed in Japanese Publication for Unexamined Patent Application No. 52-77022/1977 and (C) a method disclosed in Japanese Publication for Examined Patent Application No. 60-56694/1986 are known.

In methods (A), when the reaction is started, a large amount of catalyst in proportion to the starting material is required in order to repress the formation of undesirable by-products such as tar-like substances and naphthalene ring-scissioned by-products, including trimellitic acid, and additionally to improve the yield of 2,6-NDA. Consequently, complicated industrial processes are required in these methods in order to separate and recover the catalyst after the reaction. Moreover, in order to obtain 2,6-NDA of a high purity, a number of refining operations are necessary.

In method (B), it is disclosed that in producing terephthalic acid with a catalyst comprising cobalt, manganese and bromine in an acetic acid solvent, if a small amount (ppm) of copper is added to the acetic acid solvent, the oxidative decomposition of the acetic acid solvent is repressed. In this method, however, adding copper does not stimulate the catalytic reaction, and therefore it is hard to believe that copper contributes to the catalytic reaction. Besides, this published application does not include any statement on 2,6-NDA. In method (C) for producing terephthalic acid with a catalyst comprising copper and bromine in a water solvent, the highest yield of terephthalic acid (molar yield) is around 70 percent, and again no statement on 2,6-NDA is disclosed in this application.

As is clear from the prior art, a method of producing 2,6-NDA from dialkyl-substituted naphthalene at a high yield has not yet been fully established.

Meanwhile, diaryldicarboxylic acids are important compounds as copolymer components for the manufacture of fibers, films, plasticizers, synthetic resins etc.

Conventionally, the production of the diaryldicarboxylic acids by the oxidation of starting material with molecular oxygen in an acetic acid solvent in the presence of a catalyst comprising cobalt, manganese and bromine is known For this kind of method, for instance, the following four methods are known: (1) A method of producing diaryldicarboxylic acids by the oxidation of 4,4'-dimethylbiphenyl (see Zh. Prikl. Khim. 40 (4), 935-6 (1967)); (2) A method of producing diaryldicarboxylic acids by the oxidation of 4,4'-dimethylbiphenyl (see Japanese Publication for Unexamined Patent Applications No. 2-32041/1990 and No. 63-63638/1988); (3) A method of producing diaryldicarboxylic acids by the oxidation of 4,4'-diisopropylbiphenyl (see Japanese Publication for Unexamined Patent Application No. 63-122645/1988); and (4) A method of producing diaryldicarboxylic acids by the oxidation of 4,4'-dicyclohexylbiphenyl (see Japanese Publication for Unexamined Patent Application No. 57-16831/1982).

Also, (5) Japanese Publication for Unexamined Patent Application No. 63-310846/1988 discloses a method of producing various kinds of diaryldicarboxylic acids in the presence of the above-mentioned catalyst.

However, these methods present the following drawbacks. In method (1), 4,4'-biphenyldicarboxylic acids can be obtained at 79 mole percent yield by oxidizing 4,4'-dimethylbiphenyl with a catalyst comprising cobalt, manganese and bromine in an acetic acid solvent. However, the amount of the high-cost cobalt catalyst required is equivalent to 20 weight percent of the amount of the starting material, thereby resulting in a high production cost. Besides, 79 mole percent yield is not high enough.

In method (2), the reaction is carried out in an acetic acid solvent in the presence of a catalyst comprising cobalt, manganese and bromine, in order to obtain 4,4'-biphenyldicarboxylic acid at a high yield of at least 80 mole percent. However, since the amount of the high-cost cobalt catalyst required is equivalent to 15 weight percent of the amount of a substrate, this method also results in a high production cost.

In method (3), the reaction is carried out in an acetic acid solvent in the presence of a catalyst comprising cobalt, manganese and bromine equivalent to at least 15 weight percent of the amount of the starting material. This method achieves only a low yield of 35.8 mole percent.

In method (4), the reaction is carried out in the presence of a catalyst comprising similar catalyst components to the catalysts in methods (1), (2), (3), whose weight ratio to the starting material is at least 30 percent. However, this method also results in a low yield of 40 mole percent.

In method (5), diaryldicarboxylic acids are produced at a high yield of at least 90 mole percent by oxidizing various kinds of dialkyl-substituted diaryl compounds in the presence of a catalyst whose essential components are cobalt and bromine. However, the present inventors examined this method and found that the products had dark color. The following two reasons are listed for this cause: firstly, due to the cobalt catalyst; and secondly, the formation of large amounts of by-products which easily to color and of tar-like substances. Moreover, since the high-cost cobalt catalyst is essential in this method, industrially its production cost is not sufficiently low.

As aforesaid, in the above conventional methods, as large amounts of catalyst comprising high-cost cobalt catalyst are used, industrially sufficiently low production costs can not be achieved. Also, a method of producing diaryldicarboxylic acids having light color from the dialkyl-substituted diaryl compounds in the presence of the above-mentioned conventional catalysts with high yields of diaryldicarboxylic acids has not yet been established.

SUMMARY OF THE INVENTION

An object of the present invention is to provide a method of producing naphthalenedicarboxylic acids (NDA) efficiently by oxidizing dialkyl-substituted naphthalene under liquid phase conditions.

Another object of the present invention is to provide a method of producing 2,6-naphthalenedicarboxylic acid of a high purity at a high yield from 2,6-diisopropylnaphthalene.

A further object of the present invention is to provide a method of producing light-colored diaryldicarboxylic acids from dialkyl-substituted diaryl compounds with an improved yield of diaryldicarboxylic acids by the use of a reduced amount of a new and low-cost catalyst compared with the conventional methods.

In order to achieve the above objects, the present inventors have studied various catalysts for use as oxidation catalyst in the method of producing 2,6-NDA, and found that a catalyst comprising copper and bromine and a catalyst comprising copper, bromine and heavy metal can permit high yields of 2,6-NDA having high purity by the use of reduced amounts of catalyst compared with the case of using a standard catalyst comprising cobalt, manganese and bromine.

In addition, the above-mentioned catalysts are also effective as oxidation catalyst for the production of diaryldicarboxylic acids from dialkyl-substituted diaryl compounds.

Namely, the present invention consists in a method of producing naphthalenedicarboxylic acids of general formula (II)

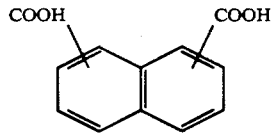

by oxidizing dialkyl-substituted naphthalene of general formula (I)

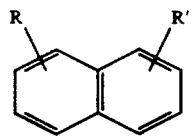

(wherein R and R' represent an alkyl group selected from the group consisting of methyl, ethyl and isopropyl groups, and wherein R and R' can be the same or different from each other), with a gas containing molecular oxygen under liquid phase conditions, and a method of producing diaryldicarboxylic acids of general formula (IV)

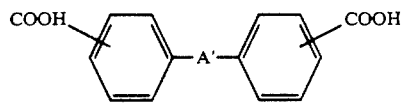

(wherein A' represents either direct bonding, O, $SO_2$ or CO)

from dialkyl-substituted diaryl compounds of general formula (III)

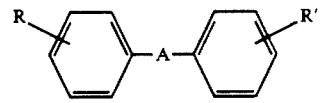

(wherein A represents either direct bonding, O, S, $SO_2$, CO or $CH_2$, R and R' respectively represent an alkyl group of 1 to 6 carbons or an alicyclic hydrocarbon group, and wherein R and R' can be the same or different from each other), both the methods using a catalyst whose active components are copper and bromine in an acetic acid solvent (the ratio of copper to bromine in numbers of atoms is from 1:0.1 to 1:100).

The present invention uses a catalyst whose active components are copper and bromine, and preferably uses catalysts of the following compositions:

1) A catalyst whose active components are copper, bromine and manganese, wherein the ratio of copper to bromine and manganese in numbers of atoms is 1:a:b, a being in the range of $0.1 \leq a \leq 100$, b being in the range of $0.1 \leq b \leq 100$.

2) A catalyst whose active components are copper, bromine, manganese and heavy metal, wherein the ratio of copper to bromine, manganese and heavy metal in numbers of atoms is 1:a:b:c, a being in the range of $0.1 \leq a \leq 100$, b being in the range of $0.1 \leq b \leq 100$, c being in the range of $0.1 \leq c \leq 100$.

3) A catalyst whose active components are copper, bromine and heavy metal, wherein the ratio of copper to bromine and heavy metal in numbers of atoms is 1:a:c, a being in the range of $0.1 \leq a \leq 100$, c being in the range of $0.1 \leq c \leq 100$.

4) A catalyst whose active components are copper, bromine and amine compound, wherein the ratio copper:bromine:amine compound, that is the ratio of the number of atoms of copper to the number of atoms of bromine and the number of moles of amine compound, is 1:a:d, a being in the range of $0.1 \leq a \leq 100$, d being in the range of $0.1 \leq d \leq 100$.

5) A catalyst whose active components are copper, bromine, amine compound and heavy metal, wherein the ratio copper:bromine:amine compound:heavy metal, that is the ratio of the number of atoms of copper to the number of atoms of bromine, the number of moles of amine compound and the number of atoms of heavy metal, is 1:a:d:e, being in the range of $0.1 \leq a \leq 100$, and d being in the range of $0.1 \leq d \leq 100$, e being in the range of $0.1 \leq e \leq 100$.

As for copper constituting these catalysts, for example, the following are listed: salts formed from copper and carboxylic acids such as formic acid, acetic acid and naphthenic acid; organic compounds such as acetylacetonate complex with copper, etc.; and inorganic compounds formed from copper and hydroxide, oxide, chloride, bromide, nitrate, sulfate or the like. These copper salts can be either anhydrous salts or hydrate salts.

Regarding bromine, a variety of bromine compounds, such as hydrogen bromide, ammonium bromide and metallic bromide, are listed.

For heavy metal in the catalysts of 2), 3) and 5), at least one kind of metallic element selected from the group consisting of vanadium, manganese, iron, cobalt, nickel, palladium and cerium, is used, and most preferably cobalt and manganese are used. Further, for the compounds, salts similar to the above-mentioned copper compounds are used.

Regarding amine compounds in the catalysts of 4) and 5), for example, the following are listed: heterocyclic amine compounds, such as pyridine, pyrazine, piperazine, picoline, lutidine, and quinoline; and alkyl amines having liquid state at room temperature, such as ethylenediamine, monopropylamine, dipropylamine, monobutylamine and dibutylamine. By considering the stability under oxidation conditions, pyridine, pyrazine, quinoline are listed as suitable amine compounds, and the most suitable one is pyridine.

The reaction according to the present invention is carried out in an organic solvent. Economically, and by considering the stability with respect to oxidation, a pure acetic acid solvent is used most preferably. However, the acetic acid solvent may be mixed with an aromatic solvent such as benzene, and aliphatic monocarboxylic acids for example propionic acid if necessary.

In the present invention, the dialkyl-substituted diaryl compounds of formula (III) illustrated above is oxidized to the diaryldicarboxylic acid of formula (IV) also illustrated. R and R' in formula (III) are oxidized to a COOH group. When A in formula (III) is S or $CH_2$, S and $CH_2$ are also oxidized to $SO_2$ and CO respectively. In the mean time, if A in this formula is either direct bonding, O, $SO_2$, or CO, A' in formula (IV) is the same as A.

As dialkyl-substituted diaryl compounds, dialkyl-substituted diaryl having an alkyl group of 1 to 6 carbons and alicyclic hydrocarbon group as a substitution group are listed. More specifically, the following will give some examples of dialkyl-substituted diaryl compound and obtainable diaryldicarboxylic acid: 4,4'-dimethylbiphenyl and 4,4'-biphenyldicarboxylic acid; 3,3'-dimethylbiphenyl and 3,3'-biphenyldicarboxylic acid; 3,4'-dimethylbiphenyl and 3,4'-biphenyldicarboxylic acid; 4,4'-diethylbiphenyl and 4,4'-biphenyldicarboxylic acid; 3,3'-diethylbiphenyl and 3,3'-biphenyldicarboxylic acid; 3,4'-diethylbiphenyl and 3,4'-biphenyldicarboxylic acid; 4,4'-diisopropylbiphenyl and 4,4'-biphenyldicarboxylic acid; 3,3'-diisopropylbiphenyl and 3,3'-biphenyldicarboxylic acid; 3,4'-diisopropylbiphenyl and 3,4'-biphenyldicarboxylic acid; 4,4'-dicyclohexylbiphenyl and 4,4'-biphenyldicarboxylic acid; 4,4'-dimethyldiphenyl ether and 4,4'-diphenyl ether dicarboxylic acid; 4,4'-dimethylbenzophenone and 4,4'-benzophenone dicarboxylic acid; 3,3'-dimethylbenzophenone and 3,3'-benzophenone dicarboxylic acid; 4,4'-dimethyldiphenyl sulfone and 4,4'-diphenylsulfone dicarboxylic acid; 4,4'-dimethyldiphenyl sulfide and 4,4'-diphenylsulfone dicarboxylic acid; and bis(4-methylphenyl) methane and 4,4'-benzophenone dicarboxylic acid.

The production of naphthalenedicarboxylic acids and diaryldicarboxylic acids according to the present invention is carried out through either of the following two methods, (i) and (ii).

In method (i), naphthalenedicarboxylic acids or diaryldicarboxylic acids is produced through the following process: placing a predetermined amount of solvent, of starting material and of catalyst into a reaction vessel; suppling a gas containing molecular oxygen to the reaction vessel, stirring the mixture under a pressure of the gas at a predetermined temperature, and carrying out a reaction.

In method (ii), naphthalenedicarboxylic acids or diaryldicarboxylic acids is produced through the following process: placing a predetermined amount of solvent and of catalyst into a reaction vessel; suppling a gas containing molecular oxygen to the reaction vessel while adding a starting material to the reaction vessel successively or intermittently, stirring the mixture under a pressure of the gas at a predetermined temperature, and carrying out a reaction. Here, the reaction may be carried out by introducing a part of the starting material into the reaction vessel in advance, or the reaction may continuously proceed by withdrawing some parts of the produced naphthalenedicarboxylic acids or diaryldicarboxylic acids from the reaction mixture.

As for the amount of catalyst used in the present invention, it equals 0.01 weight percent to 20 weight percent of the solvent, and more preferably from 0.5 weight percent to 5 weight percent thereof. A catalyst concentration lower than this range will not achieve a good activation, and a catalyst concentration higher than this range will deteriorate its solubility and increase the formation of by-products, and therefore it is undesirable to use a catalyst beyond this range.

Regarding a gas containing molecular oxygen, although air is the most suitable source industrially, oxygen and a mixed gas formed by diluting oxygen with an intert gas may also be used.

In the case of using air, it is desirable to set the reaction temperature between 150° C. and 220° C., i.e. in this temperature range the reaction can promptly proceed and the formation of undesirable by-products such as tar-like substances and carbide is restrained.

Meanwhile, in the case of using air, suitable reaction pressures range from 5 kg/cm² to 50 kg/cm² in which the mixture is maintained in liquid phase, and the most preferable reaction pressures range from 10 kg/cm² to 40 kg/cm².

The following examples will explain the present invention in more detail, however the present invention is not restricted to these examples.

DETAILED DESCRIPTION OF THE PREFERRED EMBODIMENTS

The conversion of starting materials, the yield of naphthalenedicarboxylic acids, the yield of trimellitic acid (hereinafter referred to as TMA) which is an undesirable by-product, and the yield of diaryldicarboxylic acid in EXAMPLES and COMPARATIVE EXAMPLES were determined based on the following definitions.

Conversion (%) =

$$\frac{\text{number of moles of consumed starting material}}{\text{number of moles of supplied starting material}} \times 100$$

NDA yield (%) =

$$\frac{\text{number of moles of produced NDA}}{\text{number of moles of supplied starting material}} \times 100$$

TMA yield (%) =

$$\frac{\text{number of moles of produced TMA}}{\text{number of moles of supplied starting material}} \times 100$$

Yield of diaryldicarboxylic acid (%) =

$$\frac{\text{number of moles of produced diaryldicarboxylic acid}}{\text{number of moles of supplied starting material}} \times 100$$

EXAMPLE 1

In this example, a reaction was carried out according to method (ii) described above. More specifically, 300 g of acetic acid, and 2 g of copper acetate [Cu(OAc)$_2$] and 3 g of KBr as catalyst were placed into a titanium made 1 l autoclave equipped with a stirrer, a condenser, a gas blowing tube, a starting material supplying line and pressure-control valve. The mixture was heated to 190° C. and then pressurized to 30 kg/cm$^2$ with air.

Next, while supplying a volume of air enough for oxidation to the autoclave and while controlling the internal pressure of the autoclave at 30 kg/cm$^2$, 60.0 g of 2,6-diisopropylnaphthalene (hereinafter referred to as 2,6-DIPN) was added to the mixture in five hours stepwise to commence the reaction. Only air was supplied to therein for another one hour to proceed the reaction, and then the reaction was terminated.

The reaction product was analyzed with liquid chromatography. The analysis resulted in 100 percent conversion of 2,6-DIPN, 70 percent yield of 2,6-NDA and 27 percent yield of TMA as shown in Table 2.

EXAMPLES 2 TO 19

Here, reactions were carried out under the same conditions as in EXAMPLE 1, except that the components and composition of catalyst were respectively changed as shown in Table 1 and the reaction temperature and pressure were also changed as shown in Table 2. The reaction conditions and results are respectively shown in Table 1 and Table 2.

As is clear from the results of EXAMPLES 1 to 19, high yields of 2,6-NDA, at least 70 percent, were achieved with small amounts of catalyst less than 15 percent of the amount of the starting material. Thus, the yield of 2,6-NDA was improved with reduced amounts of catalyst compared with conventional cases.

The results show that at least one kind of heavy metallic element selected from the group consisting of vanadium, manganese, iron, cobalt, nickel, palladium and cerium can be used as heavy metal in catalyst, and more preferably cobalt and manganese will be used.

EXAMPLE 20

2,6-NDA was produced according to method (ii) explained above.

A reaction was carried out under the same conditions as in EXAMPLE 1, except that 250 g of benzene as solvent and 3.53 g of cupric bromide and 2.50 g of pyridine as catalyst were respectively used.

The analysis of the reaction product yielded the following results. As shown in Table 4, the conversion of 2,6-DIPN was 100 percent, the yield of 2,6-NDA was 62 percent, and the yield of TMA was 28 percent.

EXAMPLES 21 TO 24

Nitrobenzene, o-dichlorobenzene, acetic acid, and a mixture of benzoic acid and water (4:1) were respectively used as solvent instead of benzene used in EXAMPLE 20, and the reaction temperature and pressure were varied as shown in Table 4. Except for these differences, reactions were carried out under the same conditions as in EXAMPLE 20. The reaction conditions and results are respectively presented in Table 3 and Table 4. The results of EXAMPLES 20 to 24 show a variety of 2,6-NDA yields which may be due to differences in the solubility of the catalyst in each solvent. According to the results, the highest 2,6-NDA yield was obtained when acetic acid was used as solvent.

EXAMPLE 25

25.0 g of cupric bromide was dissolved in 200 ml of ethanol, and heated to 50° C. To this solution, an ethanol solution containing 22.1 g of pyridine which was heated up to 50° C. was added, so that a precipitate was formed. The precipitate was separated from the reaction mixture by filtration, and then dried overnight under reduced pressure at a temperature of 45° C. to obtain 40.5 g of a first complex (CuBr$_2$Py$_2$) composed of copper, bromine and pyridine.

In this example, a reaction was carried out under the same conditions as in EXAMPLE 20, except that 3.0 g of the obtained first complex was used as catalyst. The reaction conditions and results are respectively shown in Table 3 and Table 4.

EXAMPLE 26 TO EXAMPLE 29

Nitrobenzene, o-dichlorobenzene, acetic acid, and a mixture of benzoic acid and water (4:1) were respectively used as solvent instead of benzene used in EXAMPLE 25, and the reaction temperature and pressure were respectively varied as shown in Table 4. Except for these differences, reactions were carried out under the same conditions as in EXAMPLE 25. The reaction conditions and results are respectively presented in Table 3 and Table 4.

In EXAMPLES 25 to 29, the first complex as catalyst had improved solubility in every solvent other than acetic acid, and therefore yields of 2,6-NDA which were similar to the yield obtained with acetic acid were achieved with the respective solvents.

EXAMPLE 30

1.76 g of cupric bromide, 1.73 g of cobalt bromide and 2.5 g of pyridine were used as catalyst, and the reaction temperature and time were respectively set at 180° C. and for seven hours. Except for these differences, a reaction was carried out under the same conditions as in EXAMPLE 20. The reaction conditions and results are respectively given in Table 5 and Table 6.

EXAMPLE 31

A reaction was carried out under the same conditions as in EXAMPLE 30, except that 1.70 g of manganese bromide was used instead of 1.73 g of cobalt bromide. The reaction conditions and results are respectively presented in Table 5 and Table 6. The results of EXAMPLES 30 and 31 show that adding cobalt or manganese to the catalyst in EXAMPLE 20 improves the yield of 2,6-NDA.

EXAMPLE 32

The results of EXAMPLE 25 showed that the use of complex catalyst improved the yield of 2,6-NDA with respect to various solvents, so complexes were formed from pyridine and respective copper and cobalt in the catalyst used in EXAMPLE 30. 2,6-NDA was produced with the use of the same amount of the complex catalyst as in EXAMPLE 30.

The complex catalyst containing copper was prepared according to the process explained in EXAMPLE 25, and the complex catalyst containing cobalt was also prepared in the same process except that cobalt bromide was used instead of cupric bromide. Through the preparation process, 40.2 g of a second complex ($CoBr_2Py_2$) composed of cobalt, bromine and pyridine was obtained.

A reaction was carried out under the same conditions as in EXAMPLE 20, except that a catalyst formed from 3.01 g of the first complex and 2.97 g of the second complex was used and the reaction temperature was set at 180° C. The reaction conditions and results are respectively shown in Table 5 and Table 6.

EXAMPLE 33

In this example, a third complex ($MnBr_2Py_2$) composed of manganese, bromine and pyridine was prepared with the use of manganese instead of cobalt used in EXAMPLE 32.

A reaction was carried out under the same conditions as in EXAMPLE 32, except that a mixture of 3.01 g of the first complex and 2.94 g of the third complex was used as catalyst. The reaction conditions and results are respectively presented in FIG. 5 and FIG. 6. The results of EXAMPLES 30 to 33 show that 2,6-NDA is obtained at improved yields with the use of the complex catalyst.

EXAMPLE 34

The results of EXAMPLE 32 show that the use of the complex catalyst improves the yield of an objective product that is 2,6-NDA while the yield of an undesirable by-product that is TMA is decreased. Therefore, a complex catalyst composed of copper and cobalt was prepared, and 2,6-NDA was produced in the presence of the complex catalyst.

The catalyst was prepared through the following process of obtaining 45.6 g of a fourth complex ($Cu_{0.5}Co_{0.5}Br_2Py_2$) composed of copper, cobalt, bromine and pyridine: dissolving 11.17 g of cupric bromide and 10.94 g of cobalt bromide in 200 ml of ethanol; heating the reaction mixture to 50° C.; adding 200 ml of ethanol solution containing 22.1 g of pyridine, heated to 50° C., to the mixture to form a precipitate; stirring the mixture having the precipitate for 10 minutes while controlling the temperature of the solution between 50° C. and 60° C.; cooling the mixture to room temperature; separating the precipitate from the mixture by filtration; drying the precipitate overnight under reduced pressure at a temperature of 45° C.

A reaction was carried out under the same conditions as in EXAMPLE 20, except that 4.0 g of the fourth complex was used as catalyst and the reaction temperature was set at 180° C. The reaction conditions and results are respectively shown in Table 5 and Table 6. This example achieved a high yield of 2,6-NDA and a low yield of TMA similar to EXAMPLE 32.

EXAMPLES 35 TO 39

Five kinds of complexes, i.e. fifth complex to ninth complex whose ratios of copper to cobalt were various, were obtained through the same process as in EXAMPLE 34 by using five different mixing ratios of cupric bromide and cobalt bromide. The respective mixing ratios are shown in Table 5.

Then, reactions were carried out under the same conditions as in EXAMPLE 34, except that 4.0 of the respective complexes were used as catalyst. The reaction conditions and results are respectively shown in Table 5 and Table 6. These examples also achieved high yields of 2,6-NDA and low yields of TMA similar to EXAMPLE 34.

EXAMPLES 40 AND 41

In these examples, acetic acid and a mixture of benzoic acid and water (22:3) were respectively used as solvent instead of benzene used in EXAMPLE 39. The reaction temperature was set at 200° C. in EXAMPLE 40 and the pressure was set at 25 kg/cm$^2$ in EXAMPLE 41. Except for these differences, reactions were carried out under the same conditions as in EXAMPLE 39. The reaction conditions and results are respectively shown in Table 5 and Table 6. Both the solvents contributed to high yields of 2,6-NDA and low yields of TMA like EXAMPLE 39.

COMPARATIVE EXAMPLE 1

To define that catalysts containing copper achieve higher yields of 2,6-NDA, 6.0 g of the second complex ($CoBr_2Py_2$) was solely used and the reaction time was set at eight hours. A reaction was carried out under the same conditions as in EXAMPLE 20 except for the above changes. The reaction conditions and results are respectively shown in Table 11 and Table 12. As is clear from the results of this comparative example and EXAMPLE 32, copper is an essential component for the catalyst relating to the present invention.

EXAMPLE 42

A complex catalyst was prepared by mixing copper and manganese instead of mixing copper and cobalt used in EXAMPLE 34.

The complex catalyst was prepared through the following process of obtaining 35.1 g of a tenth complex ($Cu_{0.2}Mn_{0.8}Br_2Py_2$) composed of copper, manganese, bromine and pyridine: dissolving 4.47 g of cupric bromide and 17.2 g of manganese bromide in 200 ml of ethanol; heating the reaction mixture to 50° C.; adding 220 ml of an ethanol solution containing 25.0 g of pyridine, heated up to 50° C., to the mixture to form a precipitate; stirring the mixture having the precipitate for 20 minutes while controlling the temperature of the mixture between 50° C. and 60° C.; cooling the mixture to room temperature; separating the precipitate from the mixture by filtration; drying the precipitate overnight under reduced pressure at a temperature of 45° C.

A reaction was carried out under the same conditions as in EXAMPLE 38, except that 4.0 g of the tenth complex was used as catalyst and o-dichlorobenzene was used as solvent. The solvent, reaction conditions and results are respectively shown in Table 5 and Table 6. This example achieved a high yield of 2,6-NDA and a low yield of TMA like the case where a complex catalyst composed of copper and cobalt was used.

EXAMPLES 43 TO 45

Catalysts used in these examples were prepared by respectively adding either palladium acetate, cerium acetate or nickel acetate to the complex catalyst in EXAMPLE 42. The reaction temperature and pressure were varied as shown in Table 6. Except for these differences, reactions were carried out under the same conditions as in EXAMPLE 42. The reaction conditions and results are respectively presented in Table 5 and Table 6. High yields of 2,6-NDA and low yields of TMA similar to EXAMPLES 34 to 42 were obtained even when these heavy-metallic salts were used in combination with other components of the catalyst.

COMPARATIVE EXAMPLES 2 TO 4

With the use of a well known catalyst described in the prior art, i.e. the catalyst comprising cobalt, manganese and bromine, three reactions were carried out under conditions similar to EXAMPLE 20, wherein the two reactions were carried out by the use of different amounts of catalyst and the one reaction was carried out with the use of a different solvent The solvents, reaction conditions and results are respectively presented in Table 11 and Table 12.

As is clear from the results, the objective 2,6-NDA was barely produced with benzene as solvent even when a large amount of catalyst was used.

EXAMPLES 46 TO 50

Either 4.0 g of the eighth complex ($Cu_{0.2}Co_{0.8}Br_2Py_2$) prepared in EXAMPLE 38 or 4.0 g of the tenth complex ($Cu_{0.2}Mn_{0.8}Br_2Py_2$) prepared in EXAMPLE 42 was used as catalyst, and either 60 g of 2,6-dimethylnaphthalene, 60 g of 2,6-diethylnaphthalene or 60g of 2-methyl-6-isopropylnaphthalene (hereinafter referred to as MIPN) was used as starting material. The reaction temperature and solvent were varied as shown in Table 8. Except for these differences, reactions were carried out under the same conditions as in EXAMPLE 20. The reaction conditions and results are respectively presented in Table 7 and Table 8. High yields of 2,6-NDA and low yields of TMA similar to EXAMPLES 34 to 44 were achieved with various 2,6-dialkyl-substituted naphthalenes (alkyl group represents methyl group, ethyl group or isopropyl group) as starting material and with acetic acid as solvent which was widely used as solvent in the prior art or with benzene as solvent which was not used as solvent in the prior art. Thus, the results indicate that various 2,6-dialkyl-substituted naphthalenes can be used as starting material.

EXAMPLES 51 to 53

Catalysts prepared by mixing the eighth complex ($Cu_{0.2}Co_{0.8}Br_2Py_2$) with vanadium, iron or cerium, and MIPN as starting material were used. The solvent and reaction conditions were varied as shown in Table 8. Except for these differences, reactions were carried out under the same conditions as in EXAMPLE 20. The solvents, reaction conditions and results are respectively presented in Table 7 and Table 8. High yields of 2,6-NDA and low yields of TMA similar to EXAMPLES 34 to 45 were achieved even when these heavy-metallic salts were used in combination with the other components of catalyst. The results of these EXAMPLES 51 to 53, of COMPARATIVE EXAMPLE 1 and of EXAMPLES 43 to 45 show that at least one kind of element from the group consisting of cobalt, manganese, iron, vanadium, cerium, nickel and palladium is used as heavy metal for catalysts comprising copper, bromine, pyridine and heavy metal.

EXAMPLE 54

In the process of preparing the first complex used in EXAMPLES 25 to 29, copper acetate and ammonium bromide were used instead of cupric bromide to prepare a complex catalyst.

The complex catalyst was prepared through the process of obtaining 39.2 g of a twelfth complex ($CuBr_2Py_2$): dissolving 22.4 g of copper acetate, and 21.9 g of ammonium bromide in 200 ml of ethanol; heating the reaction mixture to 50° C.; mixing 200 ml of an ethanol solution containing 22.1 g of pyridine, heated to 50° C., to the mixture to form a precipitate; separating the precipitate from the mixture by filtration; drying the precipitate overnight under reduced pressure at a temperature of 45° C.

A reaction was carried out under the same conditions as in EXAMPLE 25, except that 3.0 g of the twelfth complex was used as catalyst. The reaction conditions and results are respectively presented in Table 7 and Table 8.

The results of this example and EXAMPLE 25 show that various kinds of compounds can be used as the sources of copper and bromine.

EXAMPLE 55

A catalyst which did not form complex was used.

The compounds used for the preparation of the complex catalyst, which have the same catalyst composition as the catalyst used in EXAMPLE 40, were used instead of the catalyst in EXAMPLE 40.

A reaction was carried out under the same conditions as in EXAMPLE 40, except that 0.20 g of copper acetate [$Cu(OAc)_2H_2O$], 2.24 g of cobalt acetate [$Co(OAc)_24H_2O$], 1.96 g of ammonium bromide and 1.58 g of pyridine as catalyst were introduced to the reaction vessel, and 400 ml of acetic acid as solvent was added thereto. The reaction conditions and results are respectively shown in Table 7 and Table 8. This example resulted in a high yield of 2,6-NDA and a low yield of TMA similar to the results of EXAMPLE 40.

EXAMPLES 56 TO 58

The ratio of bromine to copper in EXAMPLE 23 was changed into 1:2.4, 1:50 and 1:100 respectively. In order to change only the mixing ratio of bromine, here copper acetate and ammonium bromide in EXAMPLE 54 were used instead of cupric bromide in EXAMPLE 23. Reactions were carried out under the same conditions as in EXAMPLE 54, except that 400 g of an acetic acid solvent was used and the ratio of bromine to copper was varied as aforesaid.

The reaction conditions and results are respectively presented in Table 7 and Table 8. These examples achieved yields of 2,6-NDA similar to the yield in EXAMPLE 23.

EXAMPLES 59 AND 60

The mixing ratio of pyridine to copper in EXAMPLE 20 was changed respectively. Except for the differences, reactions were carried out under the same conditions as in EXAMPLE 20. The reaction conditions and results are respectively shown in Table 7 and Table 8. The results present yields of 2,6-NDA similar to the yield in EXAMPLE 20.

EXAMPLE 61

A reaction was carried out in the presence of the catalyst comprising copper, bromine, pyridine and heavy metal, but the ratio of pyridine was varied from those of the catalysts of the same composition used in the above examples.

The reaction was carried out under the same conditions as in EXAMPLE 20, except that the components of catalyst shown in Table 7 and o-dichlorobenzene as solvent were used. The reaction conditions and results are respectively presented in Table 7 and Table 8.

EXAMPLES 62 TO 65

With the use of dialkyl-substituted naphthalenes other than 2,6-diisopropylnaphthalene as starting material, naphthalenedicarboxylic acids were produced.

A catalyst comprising copper, bromine and manganese was used in EXAMPLES 62 and 63, and a catalyst comprising copper, bromine, manganese and other heavy metal were used in EXAMPLES 64 and 65. The starting material was varied as shown in Table 10, and 250 g of acetic acid was used as solvent. Except for these differences, reactions were carried out under the same conditions as in EXAMPLE 1. The reaction conditions and results are respectively presented in Table 9 and Table 10.

EXAMPLE 66

A catalyst comprising copper, bromine, pyridine and manganese was used instead of the catalyst in EXAMPLE 64, and o-dichlorobenzene was used as solvent. Except for these differences, a reaction was carried out under the same conditions as in EXAMPLE 64. The reaction conditions and results are respectively shown in Table 9 and Table 10.

EXAMPLE 67

300 g of acetic acid as solvent, and 2 g of copper acetate [$Cu(OAc)_2 \cdot H_2O$] and 3 g of potassium bromide as catalyst were placed into a titanium made autoclave (1l) equipped with a stirrer, a condenser, a gas blowing tube, a starting material supplying line and a pressure-control valve. The mixture was heated to 170° C. and then pressurized to 30 kg/cm$^2$ with air. Next, while supplying air to the autoclave at a rate of 200 l/hr and while controlling the internal pressure of the autoclave at 30 kg/cm$^2$, 60.0 g of 4,4'-diisopropylbiphenyl was added to the mixture in five hours stepwise Only air was supplied for another one hour to proceed a reaction, and then the reaction was terminated.

The reaction product was analyzed with liquid chromatography. The analysis resulted in 100 percent conversion of 4,4'-diisopropylbiphenyl and 88 percent yield of 4,4'-biphenyldicarboxylic acid.

The amount of catalyst used was equivalent to 8.3 weight percent of the starting material.

EXAMPLES 68 TO 81

Reactions were carried out under the same conditions as in EXAMPLE 67, except that the catalyst and reaction temperature were respectively varied as shown in Table 13. The respective results are presented in Table 14.

EXAMPLE 82

A reaction was carried out under the same conditions as in EXAMPLE 69, except that the composition of catalyst and the amount of catalyst were respectively varied as shown in Table 13. The amount of catalyst used was equivalent to 7.7 weight percent of the starting material. The results are given in Table 14.

EXAMPLES 67 to 82 achieved high yields of 4,4'-biphenyldicarboxylic acid, at least 80 percent, with the use of small amounts of catalyst which are less than 15 weight percent of the starting material. Thus, it is clear from the results that the yield of 4,4'-biphenyldicarboxylic acid is improved with reduced amounts of catalyst compared to the prior art.

When manganese, iron, nickel, palladium and cerium were used as the components of the catalyst, a slightly colored crude cake was resulted after the reaction. Meanwhile, when cobalt and vanadium were used, the resulting crude cake was light yellow.

EXAMPLE 83 TO 85

Reactions were carried out under the same conditions as in EXAMPLE 69, except that the ratio of each element of the catalyst comprising copper, bromine and manganese was varied. The reaction conditions and results are respectively given in Table 13 and Table 14.

EXAMPLE 86 AND 87

Reactions were carried out under the same conditions as EXAMPLE 69, except that a catalyst comprising copper, bromine, manganese and heavy metal (iron or cerium) was used. The reaction conditions and results are respectively presented in Table 13 and Table 14.

EXAMPLE 88

4,4'-dimethylbiphenyl was used as starting material instead of 4,4'-diisopropylbiphenyl, and the composition of catalyst and the amount of catalyst were respectively varied as shown in Table 15. Except for these differences, a reaction was carried out under the same conditions as in EXAMPLE 69. The amount of catalyst used was equivalent to 2.7 weight percent of the starting material. The results are shown in Table 16.

EXAMPLE 89

4,4'-dimethylbiphenyl was used as starting material instead of 4,4'-diisopropylbiphenyl, and the composition of catalyst and the amount of catalyst were varied as shown in Table 15. Except for these differences, a reaction was carried out under the same conditions as in EXAMPLE 74. The amount of catalyst used was equivalent to 2.7 weight percent of the starting material. The results are shown in Table 16.

EXAMPLE 90

4,4'-dimethylbiphenyl was used as starting material instead of 4,4'-diisopropylbiphenyl, and 0.1 g of copper acetylacetonate [$Cu(AA)_2$], 0.57 g of ammonium bromide and 0.57 g of cobalt acetate [$Co(OAc)_2 \cdot 4H_2O$] as catalyst were used. Except for these differences, a reaction was carried out under the same conditions as in EXAMPLE 76. The amount of catalyst used was equivalent to 2.1 weight percent of the starting material. The reaction conditions and results are respectively shown in Table 15 and Table 16.

EXAMPLE 91

A reaction was carried out under the same conditions as in EXAMPLE 88, except that 4,4'-diethylbiphenyl was used as starting material instead of 4,4'-dimethylbiphenyl. The reaction conditions and results are respectively shown in Table 15 and Table 16.

EXAMPLE 92

A reaction was carried out under the same conditions as in EXAMPLE 89, except that 4,4'-diethylbiphenyl was used as starting material instead of 4,4'-dimethylbiphenyl. The reaction conditions and results are respectively shown in Table 15 and Table 16.

EXAMPLE 93

A reaction was carried out under the same conditions as in EXAMPLE 90, except that 4,4'-diethylbiphenyl was used as starting material instead of 4,4'-dimethylbiphenyl. The reaction conditions and results are respectively shown in Table 15 and Table 16.

EXAMPLE 94

A reaction was carried out under the same conditions as in EXAMPLE 88, except that 4,4'-dimethyldiphenyl ether was used as starting material instead of 4,4'-dimethylbiphenyl. The reaction conditions and results are respectively shown in Table 15 and Table 16.

EXAMPLE 95

A reaction was carried out under the same conditions as in EXAMPLE 89, except that 4,4'-dimethyldiphenyl ether was used as starting material instead of 4,4'-dimethylbiphenyl. The reaction conditions and results are respectively shown in Table 15 and Table 16.

EXAMPLE 96

A reaction was carried out under the same conditions as in EXAMPLE 88, except that 4,4'-dimethyldiphenyl sulfone was used as starting material instead of 4,4'-dimethylbiphenyl. The reaction conditions and results are respectively shown in Table 15 and Table 16.

EXAMPLE 97

A reaction was carried out under the same conditions as in EXAMPLE 89, except that 4,4'-dimethyldiphenyl sulfone was used as starting material instead of 4,4'-dimethylbiphenyl. The reaction conditions and results are respectively shown in Table 15 and Table 16.

EXAMPLE 98

A reaction was carried out under the same conditions as in EXAMPLE 88, except that 4,4'-dimethylbenzophenone was used as starting material instead of 4,4'-dimethylbiphenyl. The reaction conditions and results are respectively shown in Table 15 and Table 16.

EXAMPLE 99

A reaction was carried out under the same conditions as in EXAMPLE 89, except that 4,4'-dimethylbenzophenone was used as starting material instead of 4,4'-dimethylbiphenyl. The reaction conditions and results are respectively shown in Table 15 and Table 16.

EXAMPLES 88 to 99 achieved high yields, at least 90 percent, of 4,4'-biphenyldicarboxylic acid with the use of small amounts of catalyst which were respectively equivalent to 2.1 weight percent and 2.7 weight percent of the starting material when 4,4'-diethylbiphenyl, 4,4'-dimethyldiphenyl ether, 4,4'-dimethyldiphenyl sulfone and 4,4'-dimethylbenzophenone were used as starting material. Thus, the results show that the yield of 4,4'-biphenyldicarboxylic acid is improved with reduced amounts of catalyst compared with the prior art.

EXAMPLES 100 AND 101

The catalysts given in Table 15 and the isomer of 4,4'-diisopropylbiphenyl as starting material were used. Except for these differences, reactions were carried out under the same conditions as in EXAMPLE 67. The reaction conditions and results are respectively presented in Table 15 and Table 16.

EXAMPLES 102 TO 106

Various catalysts comprising copper, bromine, pyridine and/or heavy metal shown in Table 17 were respectively used. As for solvent, benzene was used in EXAMPLES 102 to 104 and o-dichlorobenzene was used in EXAMPLES 105 and 106. Except for these differences, reactions were carried out under the same conditions as in EXAMPLE 67. The reaction conditions and results are respectively presented in Table 17 and Table 18.

EXAMPLES 107 and 109

The catalysts comprising copper, bromine, pyridine and heavy metal and the solvents given in Table 18 were respectively used. 4,4'-diisopropylbiphenyl and its isomer were respectively used as starting material. The reaction conditions and results are respectively shown in Table 17 and Table 18.

COMPARATIVE EXAMPLE 5

A reaction was carried out in the presence of a conventional catalyst so as to compare it with the reaction carried out in the presence of the catalyst relating to the present invention.

More specifically, 9.0 g (equivalent to 15 weight percent of the starting material) of the catalyst comprising cobalt, manganese and bromine presented in Table 19 was used as the conventional catalyst. Except this, the reaction was carried out under the same conditions as in EXAMPLE 67. The reaction conditions and results are respectively shown in Table 19 and Table 20.

The resulted yield of 4,4'-biphenyldicarboxylic acid was lower than the yield in EXAMPLE 67.

It was found from an observation, although not given in the table, that the reaction product contained many tar-like substances which seemed to be by-products and the obtained 4,4'-biphenyldicarboxylic acid was dark brown.

COMPARATIVE EXAMPLE 6

A reaction was carried out under the same conditions as in EXAMPLE 68, except that copper acetate was omitted. The reaction conditions and results are respectively shown in Table 19 and Table 20.

The yield of 4,4'-biphenyldicarboxylic acid in this example is lower than the yield in EXAMPLE 69. Thus, the results present that copper is an essential component for the catalyst of the present invention.

COMPARATIVE EXAMPLE 7

A reaction was carried out under the same conditions as in EXAMPLE 69, except that potassium bromide was omitted and 9.0 g of manganese acetate was used. The reaction conditions and results are respectively given in Table 19 and Table 20.

The conversion of the starting material according to this reaction was relatively low, 64 percent, and the yield of 4,4'-biphenyldicarboxylic acid was also low, 7 percent. From the results, it is clear that bromine is an essential component for the catalyst of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

| Example No. | Components of Catalyst (g) | | | | Composition (atom ratio) | | | |
|---|---|---|---|---|---|---|---|---|
| | | | | | Cu | Br | Mn | Heavy Metal |
| 1 | Cu(OAc)$_2$H$_2$O, (2.0) | KBr, (3.0) | — | — | 1 | 2.5 | — | — |
| 2 | Cu(OAc)$_2$H$_2$O, (0.4) | KBr, (3.0) | — | Co(OAc)$_2$4H$_2$O (3.0) | 1 | 12.6 | — | 6.0 |
| 3 | Cu(OAc)$_2$H$_2$O, (0.4) | KBr, (3.0) | Mn(OAc)$_2$4H$_2$O (3.0) | — | 1 | 12.6 | 6.0 | — |
| 4 | Cu(OAc)$_2$H$_2$O, (0.4) | KBr, (1.0) | — | VO(AA)$_3$ (3.0) | 1 | 4.2 | — | 6.0 |
| 5 | Cu(OAc)$_2$H$_2$O, (0.4) | KBr, (3.0) | — | Fe(AA)$_2$ (3.0) | 1 | 12.6 | — | 4.2 |
| 6 | Cu(OAc)$_2$H$_2$O, (0.4) | KBr, (0.24) | — | Pd(OAc)$_2$ (0.5) | 1 | 1.0 | — | 1.0 |
| 7 | Cu(OAc)$_2$H$_2$O, (0.4) | KBr, (3.0) | — | Ce(OAc)$_3$H$_2$O (3.0) | 1 | 12.6 | — | 4.6 |
| 8 | Cu(OAc)$_2$H$_2$O, (0.4) | NH$_4$Br, (3.0) | — | Co(OAc)$_2$4H$_2$O (3.0) | 1 | 15.4 | — | 6.0 |
| 9 | Cu(AA)$_2$, (0.53) | NH$_4$Br, (3.0) | — | Co(OAc)$_2$4H$_2$O (3.0) | 1 | 15.4 | — | 6.0 |
| 10 | Cu(AA)$_2$, (0.53) | KBr, (1.0) | Mn(OAc)$_2$4H$_2$O (3.0) | — | 1 | 4.2 | 6.0 | — |
| 11 | Cu(AA)$_2$, (0.53) | KBr, (1.0) | — | Co(AA)$_3$ (3.0) | 1 | 4.2 | — | 4.1 |
| 12 | Cu(AA)$_2$, (0.53) | KBr, (3.0) | — | Co(AA)$_3$ (3.0) | 1 | 12.6 | — | 4.1 |
| 13 | Cu(AA)$_2$, (0.53) | KBr, (3.0) | Mn(AA)$_2$ (3.0) | — | 1 | 12.6 | 5.8 | — |
| 14 | Cu(AA)$_2$, (0.53) | KBr, (3.0) | — | Ni(AA)$_2$ (3.0) | 1 | 12.6 | — | 5.8 |
| 15 | Cu(OAc)$_2$H$_2$O, (0.2) | KBr, (3.0) | Mn(OAc)$_2$4H$_2$O (5.8) | — | 1 | 25.2 | 23.6 | — |
| 16 | Cu(OAc)$_2$H$_2$O, (0.07) | KBr, (3.0) | Mn(OAc)$_2$4H$_2$O (5.8) | — | 1 | 72.0 | 67.4 | — |
| 17 | Cu(OAc)$_2$H$_2$O, (2.4) | NaBr, (0.8) | Mn(OAc)$_2$4H$_2$O (5.8) | — | 1 | 0.6 | 2.0 | — |
| 18 | Cu(OAc)$_2$H$_2$O, (0.1) | KBr, (3.0) | Mn(OAc)$_2$4H$_2$O, (4.8) | Fe(AA)$_2$ (1) | 1 | 50.3 | 39.1 | 7.8 |
| 19 | Cu(OAc)$_2$H$_2$O, (0.1) | KBr, (3.0) | Mn(OAc)$_2$4H$_2$O, (4.8) | Ce(OAc)$_3$H$_2$O (1) | 1 | 50.3 | 39.1 | 14.2 |

Ac: acetyl group, and AA: acetylacetonate group.

TABLE 2

| Example No. | Reaction Conditions | | | Conversion (%) | Yield (%) | |
|---|---|---|---|---|---|---|
| | Temperature (°C.) | Time (hr) | Pressure (kg/cm$^2$) | | 2,6-NDA | TMA |
| 1 | 190 | 6 | 30 | 100 | 70 | 27 |
| 2 | 190 | 6 | 30 | 100 | 75 | 21 |
| 3 | 190 | 6 | 30 | 100 | 73 | 22 |
| 4 | 190 | 6 | 30 | 100 | 74 | 20 |
| 5 | 190 | 6 | 30 | 100 | 71 | 25 |
| 6 | 180 | 6 | 30 | 100 | 72 | 24 |
| 7 | 190 | 6 | 30 | 100 | 71 | 23 |
| 8 | 190 | 6 | 30 | 100 | 74 | 23 |
| 9 | 190 | 6 | 30 | 100 | 75 | 20 |
| 10 | 190 | 6 | 30 | 100 | 72 | 24 |
| 11 | 200 | 6 | 30 | 100 | 76 | 20 |
| 12 | 200 | 6 | 20 | 100 | 73 | 19 |
| 13 | 200 | 6 | 20 | 100 | 71 | 21 |
| 14 | 190 | 6 | 30 | 100 | 71 | 19 |
| 15 | 190 | 6 | 30 | 100 | 80 | 16 |
| 16 | 190 | 6 | 30 | 100 | 78 | 15 |
| 17 | 190 | 6 | 30 | 100 | 75 | 19 |
| 18 | 190 | 6 | 30 | 100 | 79 | 16 |
| 19 | 190 | 6 | 30 | 100 | 78 | 15 |

300 g of acetic acid and 60 g of 2,6-diisopropylnaphthalene were respectively used as solvent and starting material in each example.
2,6-NDA: 2,6-naphthalenedicarboxylic acid, and TMA: trimellitic acid.

TABLE 3

| Example No. | Components of Catalyst (g) | Composition (atom ratio) | | |
|---|---|---|---|---|
| | | Cu | Br | Y* |
| 20 | CuBr$_2$ (3.53), Py (2.5) | 1 | 2 | 2 |

TABLE 3-continued

| Example No. | Components of Catalyst (g) | Composition (atom ratio) | | |
|---|---|---|---|---|
| | | Cu | Br | Y* |
| 21 | CuBr$_2$ (3.53), Py (2.5) | 1 | 2 | 2 |
| 22 | CuBr$_2$ (3.53), Py (2.5) | 1 | 2 | 2 |
| 23 | CuBr$_2$ (3.53), Py (2.5) | 1 | 2 | 2 |
| 24 | CuBr$_2$ (3.53), Py (2.5) | 1 | 2 | 2 |
| 25 | CuBr$_2$Py$_2$ (3.0) | 1 | 2 | 2 |
| 26 | CuBr$_2$Py$_2$ (3.0) | 1 | 2 | 2 |
| 27 | CuBr$_2$Py$_2$ (3.0) | 1 | 2 | 2 |
| 28 | CuBr$_2$Py$_2$ (3.0) | 1 | 2 | 2 |
| 29 | CuBr$_2$Py$_2$ (3.0) | 1 | 2 | 2 |

Y: amine compound, Py: pyridine, and *: number of moles.

TABLE 4

| Example No. | Solvent (g) | Reaction Conditions | | | Conversion (%) | Yield (%) | |
|---|---|---|---|---|---|---|---|
| | | Temperature (°C.) | Time (hr) | Pressure (kg/cm$^2$) | | 2,6-NDA | TMA |
| 20 | Bz (250) | 190 | 6 | 30 | 100 | 62 | 28 |
| 21 | NB (250) | 190 | 6 | 30 | 100 | 60 | 32 |
| 22 | DCB (250) | 200 | 6 | 30 | 100 | 64 | 29 |
| 23 | AcA (250) | 200 | 6 | 30 | 100 | 72 | 23 |
| 24 | BA.W (250) | 180 | 6 | 25 | 100 | 68 | 27 |
| 25 | Bz (250) | 190 | 6 | 30 | 100 | 71 | 20 |
| 26 | NB (250) | 190 | 6 | 30 | 100 | 68 | 27 |
| 27 | DCB (250) | 200 | 6 | 30 | 100 | 70 | 22 |
| 28 | AcA (250) | 200 | 6 | 30 | 100 | 73 | 19 |
| 29 | BA.W (250) | 180 | 6 | 25 | 100 | 72 | 21 |

60 g of 2,6-diisopropylnaphthalene was used as starting material in each example.
Bz: benzene, NB: nitrobenzene, DCB: o-dichlorobenzene, AcA: acetic acid, and BA.W: mixture of benzoic acid and water (4:1).

TABLE 5

| Example No. | Components of Catalyst (g) | Composition (atom ratio) | | | |
|---|---|---|---|---|---|
| | | Cu | Br | Y* | Z |
| 30 | CuBr$_2$ (1.76), CoBr$_2$ (1.73), Py (2.5) | 1 | 4 | 4 | 1 |
| 31 | CuBr$_2$ (1.76), MnBr$_2$ (1.70), Py (2.5) | 1 | 4 | 4 | 1 |
| 32 | CuBr$_2$Py$_2$ (3.01), CoBr$_2$Py$_2$ (2.97) | 1 | 4 | 4 | 1 |
| 33 | CuBr$_2$Py$_2$ (3.01), MnBr$_2$Py$_2$ (2.94) | 1 | 4 | 4 | 1 |
| 34 | Cu$_{0.5}$Co$_{0.5}$Br$_2$Py$_2$ (4.0) | 1 | 4 | 4 | 1 |
| 35 | Cu$_{0.9}$Co$_{0.1}$Br$_2$Py$_2$ (4.0) | 1 | 2.2 | 2.2 | 0.11 |
| 36 | Cu$_{0.7}$Co$_{0.3}$Br$_2$Py$_2$ (4.0) | 1 | 2.9 | 2.9 | 0.43 |
| 37 | Cu$_{0.3}$Co$_{0.7}$Br$_2$Py$_2$ (4.0) | 1 | 6.7 | 6.7 | 2.3 |
| 38 | Cu$_{0.2}$Co$_{0.8}$Br$_2$Py$_2$ (4.0) | 1 | 10 | 10 | 4 |
| 39 | Cu$_{0.1}$Co$_{0.9}$Br$_2$Py$_2$ (4.0) | 1 | 20 | 20 | 9 |
| 40 | Cu$_{0.1}$Co$_{0.9}$Br$_2$Py$_2$ (4.0) | 1 | 20 | 20 | 9 |
| 41 | Cu$_{0.1}$Co$_{0.9}$Br$_2$Py$_2$ (4.0) | 1 | 20 | 20 | 9 |
| 42 | Cu$_{0.2}$Mn$_{0.8}$Br$_2$Py$_2$ (4.0) | 1 | 10 | 10 | 4 |
| 43 | Cu$_{0.2}$Mn$_{0.8}$Br$_2$Py$_2$ (4.0), Pd(OAc)$_2$ (0.05) | 1 | 10 | 10 | 4.1 |
| 44 | Cu$_{0.2}$Mn$_{0.8}$Br$_2$Py$_2$ (4.0), Ce(OAc)$_3$H$_2$O (0.35) | 1 | 10 | 10 | 4.5 |
| 45 | Cu$_{0.2}$Mn$_{0.8}$Br$_2$Py$_2$ (4.0), Ni(OAc)$_2$4H$_2$O (0.26) | 1 | 10 | 10 | 4.5 |

Y: amine compound, Z: heavy metal, Py: pyridine, Ac: acetyl group, and *: number of moles.

TABLE 6

| Example No. | Solvent (g) | Reaction Conditions | | | Conversion (%) | Yield (%) | |
|---|---|---|---|---|---|---|---|
| | | Temperature (°C.) | Time (hr) | Pressure (kg/cm$^2$) | | 2,6-NDA | TMA |
| 30 | Bz (250) | 180 | 7 | 30 | 100 | 68 | 25 |
| 31 | Bz (250) | 180 | 7 | 30 | 100 | 66 | 26 |
| 32 | Bz (250) | 180 | 6 | 30 | 100 | 80 | 16 |
| 33 | Bz (250) | 180 | 6 | 30 | 100 | 76 | 18 |
| 34 | Bz (250) | 180 | 6 | 30 | 100 | 81 | 16 |
| 35 | Bz (250) | 180 | 6 | 30 | 100 | 75 | 19 |
| 36 | Bz (250) | 180 | 6 | 30 | 100 | 76 | 19 |
| 37 | Bz (250) | 180 | 6 | 30 | 100 | 82 | 15 |
| 38 | Bz (250) | 180 | 6 | 30 | 100 | 85 | 13 |
| 39 | Bz (250) | 180 | 6 | 320 | 100 | 84 | 13 |
| 40 | AcA (250) | 200 | 6 | 30 | 100 | 84 | 15 |
| 41 | BA.W (250) | 180 | 6 | 25 | 100 | 83 | 14 |
| 42 | DCB (250) | 180 | 6 | 30 | 100 | 80 | 16 |
| 43 | DCB (250) | 165 | 6 | 20 | 100 | 81 | 14 |
| 44 | DCB (250) | 180 | 6 | 30 | 100 | 80 | 10 |
| 45 | DCB (250) | 180 | 6 | 30 | 100 | 82 | 13 |

60 g of 2,6-isopropyl-naphthalene was used as starting material in each example.
Bz: benzene, AcA: acetic acid, DCB: o-dichlorobenzene, and BA.W: mixture of benzoic acid and water (4:1).

TABLE 7

| Example No. | Components of Catalyst (g) | Composition (atom ratio) Cu | Br | Y* | Z |
|---|---|---|---|---|---|
| 46 | $Cu_{0.2}Co_{0.8}Br_2Py_2$ (4.0) | 1 | 10 | 10 | 4 |
| 47 | $Cu_{0.2}Co_{0.8}Br_2Py_2$ (4.0) | 1 | 10 | 10 | 4 |
| 48 | $Cu_{0.2}Co_{0.8}Br_2Py_2$ (4.0) | 1 | 10 | 10 | 4 |
| 49 | $Cu_{0.2}Co_{0.8}Br_2Py_2$ (4.0) | 1 | 10 | 10 | 4 |
| 50 | $Cu_{0.2}Mn_{0.8}Br_2Py_2$ (4.0) | 1 | 10 | 10 | 4 |
| 51 | $Cu_{0.2}Co_{0.8}Br_2Py_2$ (4.0), $Fe(NO_3)_39H_2O$ (0.17) | 1 | 10 | 10 | 4.2 |
| 52 | $Cu_{0.2}Co_{0.8}Br_2Py_2$ (4.0), $NH_4VO_3$ (0.12) | 1 | 10 | 10 | 4.5 |
| 53 | $Cu_{0.2}Co_{0.8}Br_2Py_2$ (4.0), $Ce(OAc)_3H_2O$ (0.71) | 1 | 10 | 10 | 5 |
| 54 | $CuBr_2Py_2$ (3.0) | 1 | 2 | 2 | — |
| 55 | $Cu(OAc)_2H_2O$ (0.20), $NH_4Br$ (1.96), $Co(OAc)_2H_2O$ (2.24), Py (1.58) | 1 | 20 | 20 | 9 |
| 56 | $Cu(OAc)_2H_2O$ (1.58), $NH_4Br$ (1.88), Py (2.5) | 1 | 2.4 | 4 | — |
| 57 | $Cu(OAc)_2H_2O$ (0.1), $NH_4Br$ (2.4), Py (2.5) | 1 | 48.9 | 63.2 | — |
| 58 | $Cu(OAc)_2H_2O$ (0.1), $NH_4Br$ (4.8), Py (2.5) | 1 | 97.9 | 63.2 | — |
| 59 | $CuBr_2$ (3.53), $Py_2$ (1.25) | 1 | 2 | 1 | — |
| 60 | $CuBr_2$ (1.0), $Py_2$ (7.1) | 1 | 2 | 20.1 | — |
| 61 | $Cu(OAc)_2H_2O$ (0.1), KBr (3), $Mn(OAc)_24H_2O$ (4), Py (1.5) | 1 | 50.3 | 37.9 | 32.6 |

Y: amine compound, Z: heavy metal, Py: pyridine, Ac: acetyl group, and *: number of moles.

TABLE 8

| Example No. | Solvent (g) | Starting Material (g) | Temperature (°C.) | Time (hr) | Pressure (kg/cm²) | Conversion (%) | Yield(%) 2,6-NDA | TMA |
|---|---|---|---|---|---|---|---|---|
| 46 | Bz (250) | DMN (60) | 210 | 6 | 30 | 100 | 80 | 5 |
| 47 | Bz (250) | DEN (60) | 200 | 6 | 30 | 100 | 81 | 10 |
| 48 | Bz (250) | MIPN (60) | 190 | 6 | 30 | 100 | 84 | 12 |
| 49 | AcA (250) | MIPN (60) | 200 | 6 | 30 | 100 | 83 | 15 |
| 50 | Bz (250) | MIPN (60) | 190 | 7 | 30 | 100 | 80 | 14 |
| 51 | Bz (250) | MIPN (60) | 190 | 7 | 30 | 100 | 83 | 13 |
| 52 | BA.W (250) | MIPN (60) | 180 | 7 | 20 | 100 | 82 | 17 |
| 53 | DCB (250) | MIPN (60) | 180 | 7 | 30 | 100 | 80 | 9 |
| 54 | Bz (250) | DIPN (60) | 190 | 6 | 30 | 100 | 70 | 22 |
| 55 | AcA (400) | DIPN (60) | 200 | 6 | 30 | 100 | 84 | 14 |
| 56 | AcA (400) | DIPN (60) | 200 | 6 | 30 | 99 | 73 | 21 |
| 57 | AcA (400) | DIPN (60) | 200 | 6 | 30 | 100 | 75 | 13 |
| 58 | AcA (400) | DIPN (60) | 200 | 6 | 30 | 100 | 70 | 12 |
| 59 | Bz (250) | DIPN (60) | 190 | 6 | 30 | 100 | 60 | 29 |
| 60 | Bz (250) | DIPN (60) | 190 | 6 | 30 | 100 | 61 | 25 |
| 61 | DCB (250) | DIPN (60) | 190 | 6 | 30 | 100 | 68 | 23 |

Bz: benzene, AcA: acetic acid, DCB: o-dichlorobenzene, BA.W: mixture of benzoic acid and water (3:2), DMN: 2,6-dimethylnaphthalene, DEN: 2,6-diethylnaphthalene, MIPN: 2-methyl-6-isopropylnaphthalene, and DIPN: 2,6-diisopropylnaphthalene.

TABLE 9

| Example No. | Components of Catalyst (g) | | | | Composition (atom ratio) Cu | Br | Mn | Heavy Metal | Y* |
|---|---|---|---|---|---|---|---|---|---|
| 62 | $Cu(OAc)_2H_2O$ (0.1) | KBr (3.0) | $Mn(OAc)_24H_2O$ (4.8) | | 1 | 50.3 | 39.1 | — | — |
| 63 | $Cu(OAc)_2H_2O$ (0.1) | KBr (3.0) | $Mn(OAc)_24H_2O$ (4.8) | | 1 | 50.3 | 39.1 | — | — |
| 64 | $Cu(OAc)_2H_2O$ (0.1) | KBr (3.0) | $Mn(OAc)_24H_2O$ (4.8) | $Ni(AA)_2$ (1.0) | 1 | 50.3 | 39.1 | 7.7 | — |
| 65 | $Cu(OAc)_2H_2O$ (0.1) | KBr (3.0) | $Mn(OAc)_24H_2O$ (4.8) | $Ni(AA)_2$ (1.0) | 1 | 50.3 | 39.1 | 7.7 | — |
| 66 | $Cu(OAc)_2H_2O$ (0.1) | KBr (3.0) | $Mn(OAc)_24H_2O$ (3) | Py (2.5) | 1 | 50.3 | 24.4 | — | 63.2 |

Y: amine compound, Py: pyridine, Ac: acetyl group, and *: number of moles

TABLE 10

| Example No. | Solvent (g) | Starting Material (g) | Temperature (°C.) | Time (hr) | Pressure (kg/cm²) | Conversion (%) | Yield (%) |
|---|---|---|---|---|---|---|---|
| 62 | AcA | 2,7-DIPN (60) | 190 | 6 | 30 | 100 | 2,7-NDA 80 |
| 63 | AcA | 1,4-DIPN (60) | 190 | 6 | 30 | 100 | 1,4-NDA 81 |
| 64 | AcA | 2,7-DIPN (60) | 190 | 6 | 30 | 100 | 2,7-NDA 70 |
| 65 | AcA | 1,4-DIPN (60) | 190 | 6 | 30 | 100 | 1,4-NDA 69 |

TABLE 10-continued

| Example No. | Solvent (g) | Starting Material (g) | Reaction Conditions ||| Conversion (%) | Yield (%) |
|---|---|---|---|---|---|---|---|
| | | | Temperature (°C.) | Time (hr) | Pressure (kg/cm$^2$) | | |
| 66 | DCB | 2,7-DIPN (60) | 190 | 6 | 30 | 100 | 2,7-NDA 67 |

250 g of solvent was used in each example.
AcA: acetic acid, DCB: o-dichlorobenzene, DIPN: diisopropylnaphthalene, and NDA: naphthalenedicarboxylic acid.

TABLE 11

| Comparative Example No. | Components of Catalyst (g) | | | Composition (atom ratio) ||||
|---|---|---|---|---|---|---|---|
| | | | | Cu | Br | Y* | Z |
| 1 | CoBr$_2$Py$_2$ (6.0) | | | — | 2 | 2 | 1 |
| 2 | Co(OAc)$_2$4H$_2$O, (2.23) | Mn(OAc)$_2$4H$_2$O, (2.20) | KBr (2.13) | — | 1 | — | 1 |
| 3 | Co(OAc)$_2$4H$_2$O, (4.46) | Mn(OAc)$_2$4H$_2$O, (4.40) | KBr (4.26) | — | 1 | — | 1 |
| 4 | Co(OAc)$_2$4H$_2$O, (4.46) | Mn(OAc)$_2$4H$_2$O, (4.40) | KBr (4.26) | — | 1 | — | 1 |

Ac: acetyl group, Py: pyridine, Y: amine compound, Z: heavy metal, and *: number of moles.

TABLE 12

| Comparative Example No. | Solvent (g) | Reaction Conditions ||| Conversion (%) | Yield (%) ||
|---|---|---|---|---|---|---|---|
| | | Temperature (°C.) | Time (hr) | Pressure (kg/cm$^2$) | | 2,6-NDA | TMA |
| 1 | Bz (250) | 190 | 8 | 30 | 89 | 22 | 16 |
| 2 | Bz (250) | 190 | 6 | 30 | 14 | 1 | 2 |
| 3 | Bz (250) | 200 | 6 | 30 | 26 | .2 | 5 |
| 4 | AcA (250) | 200 | 6 | 30 | 100 | 62 | 25 |

Bz: benzene, and AcA: acetic acid.

TABLE 13

| Example No. | Components of Catalyst (g) | | | | Composition (atom ratio) ||||
|---|---|---|---|---|---|---|---|---|
| | | | | | Cu | Br | Mn | Heavy Metal |
| 67 | Cu(OAc)$_2$H$_2$O, (2.0) | KBr, (3.0) | — | — | 1 | 2.5 | — | — |
| 68 | Cu(OAc)$_2$H$_2$O, (0.4) | KBr, (3.0) | — | Co(OAc)$_2$4H$_2$O (3.0) | 1 | 12.6 | — | 6.0 |
| 69 | Cu(OAc)$_2$H$_2$O, (0.4) | KBr, (3.0) | Mn(OAc)$_2$4H$_2$O (3.0) | — | 1 | 12.6 | 6.0 | — |
| 70 | Cu(OAc)$_2$H$_2$O, (0.2) | KBr, (4.5) | Mn(OAc)$_2$4H$_2$O (2.0) | — | 1 | 37.8 | 8.1 | — |
| 71 | Cu(OAc)$_2$H$_2$O, (0.4) | KBr, (1.0) | — | Vo(AA)$_3$ (3.0) | 1 | 4.2 | — | 6.0 |
| 72 | Cu(OAc)$_2$H$_2$O, (0.4) | KBr, (3.0) | — | Fe(AA)$_2$ (3.0) | 1 | 12.6 | — | 4.2 |
| 73 | Cu(OAc)$_2$H$_2$O, (0.4) | KBr, (0.24) | — | Pd(OAc)$_2$ (0.5) | 1 | 1.0 | — | 1.0 |
| 74 | Cu(OAc)$_2$H$_2$O, (0.4) | KBr, (3.0) | — | Ce(OAc)$_3$H$_2$O (3.0) | 1 | 12.6 | — | 4.6 |
| 75 | Cu(OAc)$_2$H$_2$O, (0.4) | NH$_4$Br, (3.0) | — | Co(OAc)$_2$4H$_2$O (3.0) | 1 | 15.4 | — | 6.0 |
| 76 | Cu(AA)$_2$, (0.53) | NH$_4$Br, (3.0) | — | Co(OAc)$_2$4H$_2$O (3.0) | 1 | 15.4 | — | 6.0 |
| 77 | Cu(AA)$_2$, (0.53) | KBr, (1.0) | Mn(OAc)$_2$4H$_2$O (3.0) | — | 1 | 4.2 | 6.0 | — |
| 78 | Cu(AA)$_2$, (0.53) | KBr, (1.0) | — | Co(AA)$_3$ (3.0) | 1 | 4.2 | — | 4.1 |
| 79 | Cu(AA)$_2$, (0.53) | KBr, (3.0) | — | Co(AA)$_3$ (3.0) | 1 | 12.6 | — | 4.1 |
| 80 | Cu(AA)$_2$, (0.53) | KBr, (3.0) | Mn(AA)$_2$ (3.0) | — | 1 | 12.6 | 5.8 | — |
| 81 | Cu(AA)$_2$, (0.53) | KBr, (3.0) | — | Ni(AA)$_2$ (3.0) | 1 | 12.6 | — | 5.8 |
| 82 | Cu(OAc)$_2$H$_2$O, (0.1) | KBr, (0.75) | Mn(OAc)$_2$4H$_2$O (3.75) | — | 1 | 12.6 | 30.0 | — |
| 83 | Cu(OAc)$_2$H$_2$O, (0.2) | KBr, (3.0) | Mn(OAc)$_2$4H$_2$O (5.8) | — | 1 | 25.2 | 23.6 | — |
| 84 | Cu(OAc)$_2$H$_2$O, (0.07) | KBr, (3.0) | Mn(OAc)$_2$4H$_2$O, (5.8) | — | 1 | 72.0 | 67.4 | — |
| 85 | Cu(OAc)$_2$H$_2$O, | NaBr, | Mn(OAc)$_2$4H$_2$O, | | 1 | 0.8 | 2.4 | — |

TABLE 13-continued

| Example No. | Components of Catalyst (g) | | | | Composition (atom ratio) Cu | Br | Mn | Heavy Metal |
|---|---|---|---|---|---|---|---|---|
| 86 | Cu(OAc)₂H₂O, (0.1) | KBr, (3.0) | Mn(OAc)₂4H₂O, (4.8) | Fe(AA)₂ (1.0) | 1 | 50.3 | 39.1 | 7.8 |
| 87 | Cu(OAc)₂H₂O, (0.1) | KBr, (3.0) | Mn(OAc)₂4H₂O, (4.8) | Ce(OAc)₃H₂O (1.0) | 1 | 50.3 | 39.1 | 14.2 |

Ac: acetyl group, and AA: acetylacetonate group.

TABLE 14

| Example No. | Reaction Conditions Temperature (°C.) | Time (hr) | Pressure (kg/cm²) | Conversion (%) | Yield (%) |
|---|---|---|---|---|---|
| 67 | 170 | 6 | 30 | 100 | 88 |
| 68 | 170 | 6 | 30 | 100 | 90 |
| 69 | 170 | 6 | 30 | 100 | 94 |
| 70 | 160 | 6 | 30 | 100 | 90 |
| 71 | 170 | 6 | 30 | 100 | 91 |
| 72 | 170 | 6 | 30 | 100 | 90 |
| 73 | 160 | 6 | 30 | 100 | 89 |
| 74 | 170 | 6 | 30 | 100 | 91 |
| 75 | 170 | 6 | 30 | 100 | 92 |
| 76 | 170 | 6 | 30 | 100 | 91 |
| 77 | 170 | 6 | 30 | 100 | 93 |
| 78 | 180 | 6 | 30 | 100 | 90 |
| 79 | 180 | 6 | 20 | 100 | 94 |
| 80 | 180 | 6 | 20 | 100 | 95 |
| 81 | 170 | 6 | 30 | 100 | 88 |
| 82 | 170 | 6 | 30 | 100 | 80 |
| 83 | 170 | 6 | 30 | 100 | 95 |
| 84 | 170 | 6 | 30 | 100 | 93 |
| 85 | 170 | 6 | 30 | 100 | 91 |
| 86 | 170 | 6 | 30 | 100 | 92 |
| 87 | 170 | 6 | 30 | 100 | 94 |

60 g of 4,4'-diisopropylbiphenyl was used as starting material in each example. 300 g of acetic acid was used as solvent in Examples 67 to 82, and 250 g of acetic acid was used in Examples 83 to 85.

TABLE 15

| Example No. | Components of Catalyst (g) | | | | Composition (atom ratio) Cu | Br | Mn | Heavy Metal |
|---|---|---|---|---|---|---|---|---|
| 88 | Cu(OAc)₂H₂O, (0.1) | KBr, (0.75) | Mn(OAc)₂4H₂O (0.75) | — | — | 12.6 | 6.0 | — |
| 89 | Cu(OAc)₂H₂O, (0.1) | KBr, (0.75) | — | Ce(OAc)₃H₂O (0.75) | 1 | 12.6 | — | 4.6 |
| 90 | Cu(AA)₂, (0.1) | NH₄Br, (0.57) | — | Co(OAc)₂4H₂O (0.57) | 1 | 15.4 | — | 6.0 |
| 91 | Cu(OAc)₂H₂O, (0.1) | KBr, (0.75) | Mn(OAc)₂4H₂O (0.75) | — | 1 | 12.6 | 6.0 | — |
| 92 | Cu(OAc)₂H₂O, (0.1) | KBr, (0.75) | — | Ce(OAc)₃H₂O (0.75) | 1 | 12.6 | — | 4.6 |
| 93 | Cu(AA)₂, (0.1) | NH₄Br, (0.57) | — | Co(OAc)₂4H₂O (0.57) | 1 | 15.4 | — | 6.0 |
| 94 | Cu(OAc)₂H₂O, (0.1) | KBr, (0.75) | Mn(OAc)₂4H₂O (0.75) | — | 1 | 12.6 | 6.0 | — |
| 95 | Cu(OAc)₂H₂O, (0.1) | KBr, (0.75) | — | Ce(OAc)₃H₂O (0.75) | 1 | 12.6 | — | 4.6 |
| 96 | Cu(OAc)₂H₂O, (0.1) | KBr, (0.75) | Mn(OAc)₂4H₂O, (0.75) | — | 1 | 12.6 | 6.0 | — |
| 97 | Cu(OAc)₂H₂O, (0.1) | KBr, (0.75) | — | Ce(OAc)₃H₂O (0.75) | 1 | 12.6 | — | 4.6 |
| 98 | Cu(OAc)₂H₂O, (0.1) | KBr, (0.75) | Mn(OAc)₂4H₂O, (0.75) | — | 1 | 12.6 | 6.0 | — |
| 99 | Cu(OAc)₂H₂O, (0.1) | KBr, (0.75) | — | Ce(OAc)₃H₂O (0.75) | 1 | 12.6 | — | 4.6 |
| 100 | Cu(OAc)₂H₂O, (0.1) | KBr, (3) | Mn(OAc)₂4H₂O (4.8) | — | 1 | 50.3 | 39.1 | — |
| 101 | Cu(OAc)₂H₂O, (0.1) | KBr, (3) | Mn(OAc)₂4H₂O, (4.8) | Ni(AA)₂ (1.0) | 1 | 50.3 | 39.1 | 7.7 |

Ac: acetyl group, and AA: acetylacetonate group.

TABLE 16

| Example No. | Starting Material (g) | Reaction Conditions Temperature (°C.) | Time (hr) | Pressure (kg/cm²) | Conversion (%) | Yield (%) |
|---|---|---|---|---|---|---|
| 88 | DMB (60) | 170 | 6 | 30 | 100 | 96 |
| 89 | DMB (60) | 170 | 6 | 30 | 100 | 93 |
| 90 | DMB (60) | 170 | 6 | 30 | 100 | 93 |
| 91 | DEB (60) | 170 | 6 | 30 | 100 | 94 |
| 92 | DEB (60) | 170 | 6 | 30 | 100 | 91 |
| 93 | DEB (60) | 170 | 6 | 30 | 100 | 91 |
| 94 | DDE (60) | 170 | 6 | 30 | 100 | 96 |

TABLE 16-continued

| Example No. | Starting Material (g) | Reaction Conditions Temperature (°C.) | Time (hr) | Pressure (kg/cm$^2$) | Conversion (%) | Yield (%) |
|---|---|---|---|---|---|---|
| 95 | DDE (60) | 170 | 6 | 30 | 100 | 94 |
| 96 | DDS (60) | 170 | 6 | 30 | 100 | 95 |
| 97 | DDS (60) | 170 | 6 | 30 | 100 | 92 |
| 98 | DMBP (60) | 170 | 6 | 30 | 100 | 96 |
| 99 | DMBP (60) | 170 | 6 | 30 | 100 | 95 |
| 100 | 3,4'-DIPB (60) | 170 | 6 | 30 | 100 | 3,4'-BPDA 90 |
| 101 | 3,3'-DIPB (60) | 170 | 6 | 30 | 100 | 3,3'-BPDA 89 |

300 g of acetic acid was used as solvent in examples 88 to 99 and 250 g of AcOH was used in examples 100 and 101, and the yield in example 88 to 99 respectively represent the yield of 4,4'-biphenyldicarboxylic acid.
DMB: 4,4'-dimethylbiphenyl, DEB: 4,4'-diethylbiphenyl, DDE: 4,4'-dimethyldiphenyl ether, DDS: 4,4'-dimethyldiphenyl sulfone, DMBP: 4,4'-dimethylbenzophenone, DIPB: 4,4'-diisopropylbiphenyl, and BPDA: biphenyldicarboxylic acid.

TABLE 17

| Example No. | Components of Catalyst (g) | | | | Composition (atom ratio) Cu | Br | Y* | Z |
|---|---|---|---|---|---|---|---|---|
| 102 | CuBr$_2$ (3.53), Py (2.5) | | | | 1 | 2 | 2 | — |
| 103 | CuBr$_2$ (1.76), MnBr$_2$ (1.70), Py (2.5) | | | | 1 | 4 | 4 | 1 |
| 104 | Cu$_{0.1}$Co$_{0.9}$Br$_2$Py$_2$ (4.0) | | | | 1 | 20 | 20 | 9 |
| 105 | Cu$_{0.2}$Mn$_{0.8}$Br$_2$Py$_2$ (4.0) | | | | 1 | 10 | 10 | 4 |
| 106 | Cu$_{0.2}$Co$_{0.8}$Br$_2$Py$_2$ (4.0), Ce(OAc)$_3$H$_2$O (3.55) | | | | 1 | 10 | 10 | 9 |
| 107 | Cu(OAc)$_2$H$_2$O, (0.1) | KBr, (3) | Py, (1.5) | Mn(OAc)$_2$4H$_2$O (4) | 1 | 50.3 | 37.9 | 32.6 |
| 108 | Cu(OAc)$_2$H$_2$O, (0.1) | KBr, (3) | Py, (1.5) | Co(OAc)$_2$4H$_2$O (4) | 1 | 50.3 | 37.9 | 32.1 |
| 109 | Cu(OAc)$_2$H$_2$O, (0.1) | KBr, (3) | Py, (1.5) | Co(OAc)$_2$4H$_2$O (4) | 1 | 50.3 | 37.9 | 32.1 |

Y: amine compound, Z: heavy metal, Py: pyridine, Ac: acetyl group, and *: number of moles.

TABLE 18

| Example No. | Solvent (g) | Starting Material | Reaction Conditions Temperature (°C.) | Time (hr) | Pressure (kg/cm$^2$) | Conversion (%) | Yield (%) |
|---|---|---|---|---|---|---|---|
| 102 | Bz (250) | 4,4'-DIPB | 170 | 6 | 30 | 100 | 4,4'-BPDA 88 |
| 103 | Bz (250) | 4,4'-DIPB | 170 | 6 | 30 | 100 | 4,4'-BPDA 90 |
| 104 | Bz (250) | 4,4'-DIPB | 170 | 6 | 30 | 100 | 4,4'-BPDA 89 |
| 105 | DCB (250) | 4,4'-DIPB | 170 | 6 | 30 | 100 | 4,4'-BPDA 93 |
| 106 | DCB (250) | 4,4'-DIPB | 170 | 6 | 30 | 100 | 4,4'-BPDA 91 |
| 107 | DCB (250) | 4,4'-DIPB | 170 | 6 | 30 | 100 | 4,4'-BPDA 88 |
| 108 | Bz (250) | 3,4'-DIPB | 170 | 6 | 30 | 100 | 3,4'-BPDA 86 |
| 109 | Bz (250) | 3,3'-DIPB | 170 | 6 | 30 | 100 | 3,3'-BPDA 89 |

60 g of starting material was used in each example.
Bz: benzene, DCB: o-dichlorobenzene, DIPB: diisopropylbiphenyl, and BPDA: biphenyldicarboxylic acid.

TABLE 19

| Comparative Example No. | Components of Catalyst (g) | | | | Composition (atom ratio) Cu | Br | Heavy Metal |
|---|---|---|---|---|---|---|---|
| 5 | Co(OAc)$_2$4H$_2$O, (3.0) | Mn(OAc)$_2$4H$_2$O, (3.0) | KBr (3.0) | | — | 10.5 | 6.0 |
| 6 | Co(OAc)$_2$4H$_2$O, (3.0) | KBr (3.0) | | | — | 12.6 | 6.0 |
| 7 | Cu(OAc)$_2$H$_2$O, (0.4) | Mn(OAc)$_2$4H$_2$O (9.0) | | | 1 | — | 18.3 |

Ac: acetyl group.

TABLE 20

| Comparative Example No. | Reaction Conditions Temperature (°C.) | Time (hr) | Pressure (kg/cm$^2$) | Conversion (%) | Yield (%) |
|---|---|---|---|---|---|
| 5 | 170 | 6 | 30 | 100 | 40 |
| 6 | 170 | 6 | 30 | 100 | 36 |

TABLE 20-continued

| Comparative Example No. | Reaction Conditions | | | Conversion (%) | Yield (%) |
| --- | --- | --- | --- | --- | --- |
| | Temperature (°C.) | Time (hr) | Pressure (kg/cm$^2$) | | |
| 7 | 170 | 6 | 30 | 64 | 7 |

300 g of acetic acid and 60 g of 4,4'-isopropylbiphenyl were respectively used as solvent and starting material in each comparative example.

What is claimed is:

1. A method of producing naphthalenedicarboxylic acids of the formula

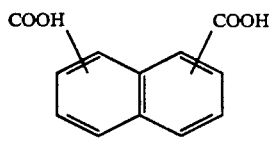

comprising:
oxidizing dialkyl-substituted naphthalene of the formula

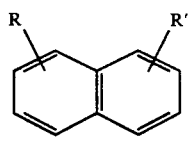

wherein R and R' respectively represent an alkyl group selected from the group consisting of methyl, ethyl and isopropyl groups, and wherein R and R' are the same or different from each other, with a gas containing molecular oxygen under liquid phase conditions in the presence of a catalyst comprising copper and bromine in an organic solvent, wherein the ratio of copper to bromine in the catalyst in numbers of atoms is 1:a, a being in the range of $0.1 \leq a \leq 100$.

2. The method of producing naphthalenedicarboxylic acids as defined in claim 1, wherein the organic solvent comprises acetic acid.

3. The method of producing naphthalenedicarboxylic acids as defined in claim 1, wherein the catalyst further comprises manganese, and wherein the ratio of the copper to the bromine and the manganese in numbers of atoms is 1a:b, a being in the range of $0.1 \leq a \leq 100$, b being in the range of $0.1 \leq b \leq 100$.

4. The method of producing naphthalenedicarboxylic acids as defined in any one of claims 1, 2 and 3, wherein the dialkyl-substituted naphthalene is 2,6-diisopropylnaphthalene.

5. The method of producing naphthalenedicarboxylic acids as defined in claim 3, wherein the catalyst further comprises at least one kind of heavy metallic element selected from the group consisting of vanadium, iron, cobalt, nickel, palladium and cerium, and wherein the ratio of the copper to the bromine, the manganese and the heavy metal in numbers of atoms is 1:a:b:c, a being in the range of $0.1 \leq a \leq 100$, b being in the range of $0.1 \leq b \leq 100$, c being in the range of $0.1 \leq c \leq 100$.

6. The method of producing naphthalenedicarboxylic acids as defined in claim 1, wherein the catalyst further comprises at least one kind of heavy metallic element selected from the group consisting of vanadium, iron, cobalt, nickel, palladium and cerium, and wherein the ratio of the copper to the bromine and the heavy metal in numbers of atoms, is 1:a:c, a being in the range of $0.1 \leq a \leq 100$, c being in the range of $0.1 \leq c \leq 100$.

7. The method of producing naphthalenedicarboxylic acids as defined in claim 1, wherein the catalyst further comprises an amine compound, and wherein the ratio of the number of atoms of the copper to the number of atoms of the bromine and the number of moles of the amine compound is 1:a:d, a being in the range of $0.1 \leq a \leq 100$, d being in the range of $0.1 \leq d \leq 100$.

8. The method of producing naphthalenedicarboxylic acids as defined in claim 7, wherein the catalyst further comprises at least one kind of heavy metallic element selected from the group consisting of vanadium, manganese, iron, cobalt, nickel, palladium and cerium, and wherein the ratio of the number of atoms of the copper to the number of atoms of the bromine, the number of moles of the amine compound and the number of atoms of the heavy metal, is 1:a:d:e, a being in the range of $0.1 \leq a \leq 100$, d being in the range of $0.1 \leq d \leq 100$, e being in the range of $0.1 \leq e \leq 100$.

9. The method of producing naphthalenedicarboxylic acids as defined in any one of claims 7 and 8, wherein the amine compound is pyridine.

10. The method for producing naphthalenedicarboxylic acids as defined in claim 1, wherein the oxidation reaction is carried out at a reaction temperature between 150° C. and 220° C.

11. The method for producing naphthalenedicarboxylic acids as defined in claim 1, wherein the oxidation reaction pressure is at least 5 kg/cm$^2$.

12. The method for producing naphthalenedicarboxylic acids as defined in claim 11, wherein the reaction pressure is in the range of 5 kg/cm$^2$ to 50 kg/cm$^2$.

13. A method of producing diaryldicarboxylic acids of the formula

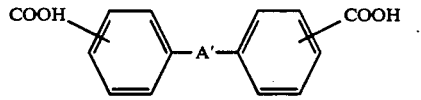

wherein A' represents either direct bonding, O, SO$_2$ or CO,
comprising:
oxidizing a dialkyl-substituted diaryl compound of the formula

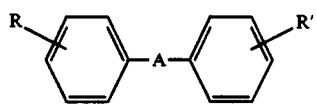

wherein A represents either direct bonding, O, S, SO$_2$, CO, or CH$_2$, and wherein R and R' respectively represent an alkyl group of 1 carbon to 6 carbons or an alicyclic hydrocarbon group, R and R' being the same or different from each other with a gas containing molecular oxygen under liquid phase conditions in the presence of a catalyst comprising copper and bromine in an organic solvent, wherein the ratio of copper to bromine in the catalyst in numbers of atoms is 1:a, a being in the range of $0.1 \leq a \leq 100$.

14. The method of producing diaryldicarboxylic acids as defined in claim 13, wherein the organic solvent comprises acetic acid.

15. The method of producing diaryldicarboxylic acids as defined in claim 13, wherein the catalyst further comprises manganese, and wherein the ratio of the copper to the bromine and the manganese in numbers of atoms is 1:a:b, a being in the range of $0.1 \leq a \leq 100$, b being in the range of $0.1 \leq b \leq 100$.

16. The method of producing diaryldicarboxylic acids as defined in any one of claims 13, 14 and 15, wherein the dialkyl-substituted diaryl compound is 4,4'-diisopropylbiphenyl.

17. The method of producing diaryldicarboxylic acids as defined in claim 15, wherein the catalyst further comprises at least one kind of heavy metallic element selected from the group consisting of vanadium, iron, cobalt, nickel, palladium and cerium, and wherein the ratio of the copper to the bromine, the manganese and the heavy metal in numbers of atoms is 1:a:b:c, a being in the range of $0.1 \leq a \leq 100$, b being in the range of $0.1 \leq b \leq 100$, c being in the range of $0.1 \leq c \leq 100$.

18. The method of producing diaryldicarboxylic acids as defined in claim 13, wherein the catalyst further comprises at least one kind of heavy metallic element selected from the group consisting of vanadium, iron, cobalt, nickel, palladium and cerium, and wherein the ratio of the copper to the bromine and the heavy metal in numbers of atoms is 1:a:c, c being in the range of $0.1 \leq a \leq 100$, c being in the range of $0.1 \leq c \leq 100$.

19. The method of producing diaryldicarboxylic acids as defined in claim 13, wherein the catalyst further comprises an amine compound, and wherein the ratio of the number of atoms of the copper to the number of atoms of the bromine and the number of moles of the amine compound is 1:a:d, c being in the range of $0.1 \leq a \leq 100$, d being the range of $0.1 \leq d \leq 100$.

20. The method of producing diaryldicarboxylic acids as defined in claim 19, wherein the catalyst further comprises at least one kind of heavy metallic element selected from the group consisting of vanadium, manganese, iron, cobalt, nickel, palladium and cerium, and wherein the ratio of the number of atoms of the copper to the number of atoms of the bromine, the number of moles of the amine compound and the number of atoms of the heavy metal is 1:a:d:e, a being in the range of $0.1 \leq a \leq 100$, d being in the range of $0.1 \leq d \leq 100$, e being in the range of $0.1 \leq e \leq 100$.

21. The method of producing diaryldicarboxylic acids as defined any one of claims 19 and 20, wherein the amine compound is pyridine.

22. The method for producing diaryldicarboxylic acids as defined in claim 13, wherein the oxidation reaction is carried out at a temperature between 150° C. and 220° C.

23. The method for producing diaryldicarboxylic acids as defined in claim 13, wherein the oxidation reaction pressure is at least 5 kg/cm$^2$.

24. The method for producing diaryldicarboxylic acids as defined in claim 23, wherein the oxidation reaction pressure is in the range of 5 kg/cm$^2$ to 50 kg/cm$^2$.

* * * * *